United States Patent [19]

Viñas

[11] Patent Number: 4,956,466
[45] Date of Patent: Sep. 11, 1990

[54] THIAZOLE DERIVATIVES AND PROCESS FOR THE PREPARATION THEREOF

[75] Inventor: Antonio B. Viñas, Barcelona, Spain

[73] Assignee: Laboratorios Viñas, S. A., Barcelona, Spain

[21] Appl. No.: 356,014

[22] Filed: May 23, 1989

[30] Foreign Application Priority Data

Jul. 11, 1988 [ES] Spain ................................. 8802172

[51] Int. Cl.$^5$ .............................................. C07F 3/06
[52] U.S. Cl. ................................................... 548/101
[58] Field of Search ......................... 548/101; 514/184

[56] References Cited

FOREIGN PATENT DOCUMENTS 59-33270 2/1984 Japan ................................. 548/101
60-04172 1/1985 Japan ................................. 548/101

*Primary Examiner*—Robert Gerstl
*Attorney, Agent, or Firm*—Dressler, Goldsmith, Shore, Sutker & Milnamow, Ltd.

[57] ABSTRACT

Thiazole derivatives of the general formula where:

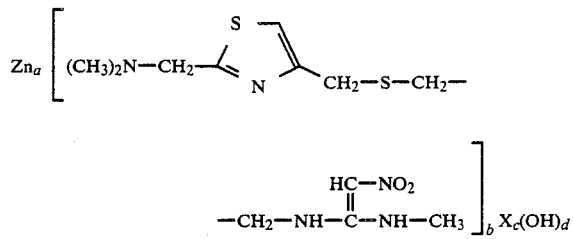

X is an anion of pharmaceutically acceptable acids;
a is an integer from 1 to 5;
b is an integer from 1 to 7;
c is 0 or an integer from 1 to 4; and
d is $2a-c$ for monovalent acid anions, is $a-c$ for divalent acid anions, and is 0 or 2 when $c=0$.

The process for the preparation of the above derivatives is based on reacting N-methyl-N'-2-((2-(dimethylaminomethyl)-4-thiazolyl) methylthio)ethyl)-2-nitro-1,1-ethylenediamine of formula II with an X anion containing zinc compound or an organozinc.

3 Claims, No Drawings

THIAZOLE DERIVATIVES AND PROCESS FOR THE PREPARATION THEREOF

DESCRIPTION

The invention relates to thiazole derivatives of the general formula I:

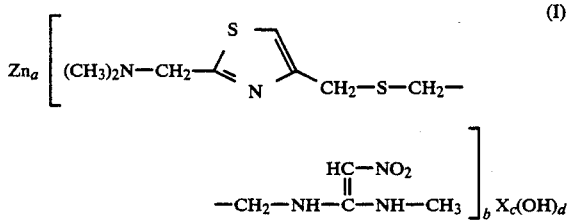

where:
X is an anion of pharmaceutically acceptable acids;
a is an integer from 1 to 5;
b is an integer from 1 to 7;
c is 0 or an integer from 1 to 4; and
d is $2a-c$ for monovalent acid anions, is $a-c$ for divalent acid anions, and is 0 or 2 when $c=0$.

The invention also relates to a process for the preparation of the derivatives of formula I, which have antiulcer properties.

Chronic gastric and duodenal ulcers are frequent disorders for which a wide range of treatments exists, including dietary measures, treatment with drugs and surgery. Among these, special attention has been paid in recent years to treatment with secretion inhibitors, one of the secretion inhibitors recently introduced being N-methyl-N'-2-((2(dimethylaminomethyl)-4-thiazolyl)-methylthio)ethyl-2-nitro-1,1-ethylenediamine of formula II (hereinafter abbreviatedly called "Nt").

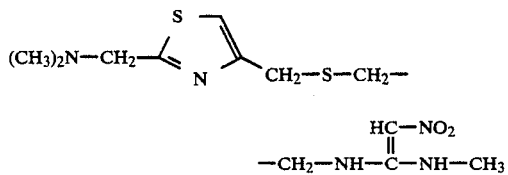

The thiazole derivatives of the present invention provide advantages on improving the antiulcer properties of the compound Nt.

In the thiazole derivatives of formula I, X may be an anion of pharmaceutically acceptabe inorganic acids such as hydrochloric acid, sulphuric acid, phosphoric acid, hydrobromic acid, hydroiodic acid and others; or an anion of non-toxic organic acids, such mono- and dicarboxylic aliphatic acids, alkanoic acids with phenyl substituents, hydroxyalkanoic acids, alkanodioic acids, aromatic acids, aromatic and aliphatic sulphonic acids and others.

Therefore, X may be chloride, bromide, iodide, flur-oide, sulphate, phosphate, chlorate, nitrate, sulphamate, maleate, fumarate, succinate, oxalate, acetate, acexamate, tartrate, citrate, camphorsulphonate, mandelate, butyno-1,4-dioate, benzoate, chlorobenzoate, methylbenzoate, hydroxybenzoate, methoxybenzoate, benzene sulphonate, toluene sulphonate, phenyl acetate, salicylate, betahydroxybutyrate, glycolate, methane sulphanate and the like.

The process of the invention is characterised in that the compound of formula II is reacted with an X anion containing zinc compound, or with an organozinc.

Said zinc compound is preferably an organic or inorganic zinc salt and the reaction is conducted in a polar organic solvent such as dimethylformamide, dimethyl sulphoxide, 1,4-dioxane, acetone, low molecular weight alcohols, etc. or in an organic aqueous mixture; preferably an alcohol will be used. The reaction temperature may reach up to the boiling point of the solvent, preferably from room temperature to 60° C. According to the type of compound it is wanted to isolate, an alkali or alkali earth hydroxide may be added at the end to alkaline pH, preferably to pH 8. Water may also be added when the reaction has been conducted in an organic solvent alone.

The compounds are obtained in solid form or in the form of a thick oil which, after removal of the solvent at reduced pressure, becomes a solid.

The compounds of formula I has shown a potent antiulcer activity. Thus, inhibition of histamine-induced gastric secretion in rats "in vivo" after intraperitoneal administration of the present Zn-thiazole compounds at a dose of 1 to 10 mg/kg, reaches pH recovery levels of 100%. The antiulcer activity in ethanol-induced ulcers in rats has proved to be satisfactory at dose levels between 100 and 250 mg/kg body weight p.o., and in certain cases total ulcer inhibition has been observed.

To facilitate the explanation, the invention is illustrated but not limited by the following example.

EXAMPLE

Preparation of $Zn(Nt)Cl_2$

A solution of 1.36 g of zinc chloride in 10 ml of ethanol was added slowly over a solution of 3.0 g of Nt in 40 ml of ethanol. After the addition, the mixture was cooled to 5° C. and held at this temperature for several hours. The solid was removed by filtration, was washed with ethanol and was dried at reduced pressure at 60° C. to give 4.0 g of product.

Elementary analysis: Calculated for $C_{12}H_{21}Cl_2N_5O_2S_2Zn$: C: 30.81; H: 4.53; Cl: 15.16; N: 14.97; S: 13.71 and Zn: 13.98. Found: C: 30.48; H: 4.88; Cl: 14.62; N: 14.69; S: 13.70 and Zn: 13.50.

IR(KBr): 3414, 1630, 1588, 1570, 1504, 1374, 1240, 983 and 756 cm$^{-1}$.

$^1$H NMR (CD$_3$OD containing 10% of CD$_3$SOCD$_3$, TMS as internal standard). Delta: 2.37 (singlet, 6H); 2.71 (triplet, 2H); 2.83 (singlet, 3H); 3.39 (triplet, 2H); 3.87 (singlet, 2H); 3.91 (singlet, 2H); 6.52 (singlet, ½H)* and 7.46 (singlet, 1H) ppm.

(*): The signal at 6.52 probably diminished due to interchange, integrated correctly in CD$_3$COCD$_3$ containing 10% of CD$_3$SOCD$_3$ for 1H).

There are described below experiments which show the therapeutic activity of $Zn(Nt)Cl_2$, referred to hereinafter as LV-200.

Antiulcer activity of compound LV-200

The antiulcer activity of LV-200 was studied on different experimental models, some of which are described below:

(A) Model of histamine-induced gastric acid secretion in rat "in vivo".

This activity was measured in Wistar rats having a body weight of $240\pm20$ g. An endovenous perfusion of a histamine solution stimulated gastric secretion, producing a reduction in the intragastric pH. Thereafter LV-200 was administered intraperitoneally and the increase of the gastric pH was evaluated. Thus, the pH recovery was 97% at a dose of 5 mg/kg.

(B) Necrotising agent model:

Using the necrotising agent model, ethanol in this case, described by Robert el al. (Gastroenterology, 77: 433, 1979), the activity of LV-200 was compared with that of Nt at equimolar dose levels and a control group which was administered vehicle.

The table below gives the lesion indices (in ulcerated area in mm) of the three groups studied, as well as the percentage inhibition of the ulcers of the treated groups over the control group (mean values±standard error of the mean).

|  | mm lesions | % inhibition |
| --- | --- | --- |
| Control | 91.2 ± 17.7 | — |
| Nt | 97.7 ± 11.8 | 0 |
| LV-200 (230 mg/kg) | 2.7 ± 1.9[a,b] | 97.1 | t test:
[a] $p < 0.01$ vs control
[b] $p < 0.001$ versus Nt

As may be seen, Nt does not inhibit ulcers induced by absolute ethanol, while practically total inhibition is obtained with LV-200.

What I claim is:

1. Thiazole derivatives of the general formula I:

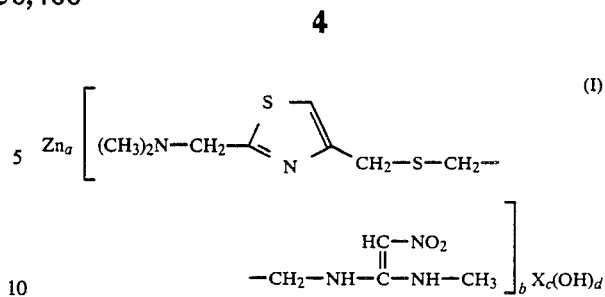

where:
X is an anion of pharmaceutically acceptable acids;
a is an integer from 1 to 5;
b is an integer from 1 to 7;
c is 0 or an integer from 1 to 4; and
d is $2a-c$ for monovalent acid anions, is $a-c$ for divalent acid anions, and is 0 or 2 when $c=0$.

2. The derivatives of claim 1, wherein the anion X is selected from the group formed by chloride, bromide, iodide, fluoride, sulphate, phosphate, chlorate, nitrate, sulphamate, maleate, fumarate, succinate, oxalate, acetate, acexamate, tartrate, citrate, camphorsulphonate, mandelate, butyno-1,4-dioate, benzoate, chlorobenzoate, methylbenzoate, hydroxybenzoate, methoxybenzoate, benzene sulphonate, toluene sulphonate, phenyl acetate, salicylate, betahydroxybutyrate, glycolate and methane sulphonate.

3. The derivatives of claim 1, wherein X is the chloride anion, $a=1$, $b=1$, $c=2$ and $d=0$.

* * * * *